(12) United States Patent
Michel et al.

(10) Patent No.: US 11,623,213 B2
(45) Date of Patent: Apr. 11, 2023

(54) MICROBIOLOGICAL TESTING DEVICE, METHOD FOR PROVISION AND USE OF SUCH A DEVICE

(71) Applicant: BIOMÉRIEUX SA, Marcy l'Etoile (FR)

(72) Inventors: Florian Michel, Chaponost (FR); Frédéric Foucault, Marcy l'Etoile (FR); Christine Rozand, Saint-Genis-les-Ollières (FR)

(73) Assignee: BIOMÉRIEUX SA, Marcy l'Etoile (FR)

( * ) Notice: Subject to any disclaimer, the term of this patent is extended or adjusted under 35 U.S.C. 154(b) by 523 days.

(21) Appl. No.: 16/492,972

(22) PCT Filed: Apr. 10, 2018

(86) PCT No.: PCT/FR2018/050902
§ 371 (c)(1),
(2) Date: Sep. 11, 2019

(87) PCT Pub. No.: WO2018/189478
PCT Pub. Date: Oct. 18, 2018

(65) Prior Publication Data
US 2020/0078782 A1     Mar. 12, 2020

(30) Foreign Application Priority Data

Apr. 13, 2017  (FR) ........................ 1753250

(51) Int. Cl.
*C12M 1/12*  (2006.01)
*C12Q 1/06*  (2006.01)
*B01L 3/00*  (2006.01)

(52) U.S. Cl.
CPC ............. *B01L 3/502* (2013.01); *C12M 25/02* (2013.01); *C12Q 1/06* (2013.01);
(Continued)

(58) Field of Classification Search
CPC . C12M 25/02; B01L 2300/0681; B01L 3/502; B01L 2200/0621; B01L 2200/0668;
(Continued)

(56) References Cited

U.S. PATENT DOCUMENTS 2,677,646 A    5/1954  Mai et al.
6,287,849 B1*  9/2001  McNerney ............. C12M 45/03
                                                   435/287.1
(Continued)

FOREIGN PATENT DOCUMENTS

EP    1783494 A1    5/2007
FR    1138452 A     6/1957
GB    2268187 A     1/1994

OTHER PUBLICATIONS

May 24, 2018 Written Opinion issued in International Patent Application No. PCT/FR2018/050902.
(Continued)

*Primary Examiner* — David W Berke-Schlessel
*Assistant Examiner* — Trent R Clarke
(74) *Attorney, Agent, or Firm* — Oliff PLC (57) ABSTRACT

A microbiological testing device for testing a liquid to be analysed that is liable to contain at least one microorganism, includes a closed inner space, a microbiological filtration member and an inlet port. The device has a nutritive layer in contact with the filtration member, and in that, in a configuration for providing the device an open/close member of the inlet port is in a closed state; the absolute gas pressure inside the closed inner space is strictly less than the standard atmospheric pressure, such that the device is able to create suction through the inlet port during a first opening of the open/close member.

22 Claims, 4 Drawing Sheets

(52) U.S. Cl.
CPC .......... *B01L 2200/0621* (2013.01); *B01L 2200/0668* (2013.01); *B01L 2200/0689* (2013.01); *B01L 2300/049* (2013.01); *B01L 2300/0681* (2013.01); *B01L 2300/0832* (2013.01); *B01L 2300/0864* (2013.01); *B01L 2300/12* (2013.01); *B01L 2300/14* (2013.01); *B01L 2400/049* (2013.01)

(58) Field of Classification Search
CPC ..... B01L 2200/0689; B01L 2300/0864; B01L 2300/14; B01L 2400/049; C12Q 1/06
See application file for complete search history.

(56) References Cited

U.S. PATENT DOCUMENTS

| | | | |
|---|---|---|---|
| 7,947,224 B2* | 5/2011 | Tashiro | B01L 3/502 |
| | | | 422/404 |
| 2014/0342447 A1 | 11/2014 | Aviles et al. | |
| 2015/0072377 A1 | 3/2015 | Browne et al. | |
| 2015/0176048 A1* | 6/2015 | Flandrois | C12M 25/02 |
| | | | 435/30 |
| 2016/0348055 A1 | 12/2016 | Liu | |

OTHER PUBLICATIONS

May 24, 2018 International Search Report issued in International Patent Application No. PCT/FR2018/050902.

* cited by examiner

MICROBIOLOGICAL TESTING DEVICE, METHOD FOR PROVISION AND USE OF SUCH A DEVICE

The present invention relates generally to the field of microbiological analysis. It relates more particularly to a microbiological testing device for testing a liquid to be analysed, this liquid being liable to contain at least one microorganism. It also relates to a process for providing such a device and to uses of such a device in a process for testing a liquid to be analysed, which is liable to contain at least one microorganism.

The invention more particularly targets the field of food-processing, pharmaceutical or cosmetic industrial microbiological testing.

The invention was developed following research that benefited from the participation of the *Centre National d'Etudes Spatiales* (CNES) [French National Center for Space Studies].

There are numerous situations in which it is sought to test the presence of at least one microorganism in a liquid, generally with a view to being able to note the absence of this microorganism.

Of course, the liquid to be analysed may be a biological fluid (whole blood, serum, plasma, urine, cerebrospinal fluid, organ secretion, etc.). Nonetheless, the liquid may also be an industrial liquid, especially a food liquid (water, beverages in general and especially fruit juices, milk, soda, etc.) or a pharmaceutical or cosmetic liquid.

Numerous laboratory techniques are known which make it possible to filter the liquid to be analysed in order to collect microorganisms potentially contained in the liquid, to culture these microorganisms in order subsequently to be able to detect them, count them, characterize them and/or identify them. These techniques require a certain number of handling operations that are well known to laboratory technicians.

In these techniques, it is often required to use a filtration device which comprises a closed inner space delimited by a chamber and which is configured to receive the liquid to be analysed. Such a technique is especially referred to as "membrane filtration". A microbiological filtration member, for example a filtering membrane, is arranged in the closed inner space and separates, in the closed inner space, a first compartment from a second compartment of the closed inner space. The device comprises an inlet port for the liquid to be analysed, which opens into the first compartment of the closed inner space.

In the known filtration devices, such as those of document EP-1.783.494, a suction port is provided which is configured to be connected to an external source of suction. In the use of such a device, it is therefore necessary to connect the external source of suction to the suction port in order to generate, when the liquid to be analysed is introduced into the device via the inlet port, a negative pressure inside the closed inner space, this negative pressure promoting, or even being necessary for, filtration.

Once the filtration has been carried out, the microorganisms being retained on the filtration member, the device is opened to recover the filtration member which is transferred into a culturing device to enable the incubation of the microorganisms.

Such a technique is easy to carry out in a laboratory.

However, such a technique is difficult to carry out in an operational environment, especially in an industrial environment in which liquids are produced, packaged, distributed or used. Indeed, in this context, it is beneficial to be able to have elements for detecting a potential contamination of the liquid by an undesired microorganism. However, the usual techniques as described above require transporting a sample of liquid to be analysed to a laboratory where the usual methods can be carried out. Indeed, it is difficult to envision carrying out these usual operations in situ at the industrial site for production, packaging, distribution or use of the liquid. This is because the handling of a contaminated liquid in such an environment would pose a risk of propagating the contamination if incorrectly handled. Moreover, the step of culturing any microorganisms, which may be present, requires the presence of a nutritive medium, which by definition promotes the growth of the microorganisms. It is of course undesirable that such a nutritive medium is introduced in such an industrial context. Furthermore, the usual techniques for detection also require protecting the sample to be analysed from any external contamination, thus working in as sterile an environment as possible to avoid false positives.

The aim of the invention is therefore that of proposing a device and a process for microbiological testing of a liquid to be analysed which enable particularly simplified testing operations that it would even be possible to envision using or carrying out outside of a microbiology laboratory, including in an industrial environment.

To this end, the invention firstly proposes a microbiological testing device for testing a liquid to be analysed that is liable to contain at least one microorganism, of the type comprising:

- a closed inner space delimited by a chamber and configured to receive the liquid to be analysed;
- a microbiological filtration member arranged in the closed inner space and separating, in the closed inner space, a first compartment from a second compartment of the closed inner space;
- an inlet port for the liquid to be analysed, the inlet port opening into the first compartment of the closed inner space.

Such a device is characterized in that, in a configuration for providing the microbiological testing device before use, the microbiological testing device comprises, inside the closed inner space, a nutritive layer comprising a composition of a microbiological culture medium, the nutritive layer being in contact with the filtration member, in that the inlet port of the microbiological testing device comprises an open/close member, and in that, in the configuration for providing the microbiological testing device before use:

- the open/close member of the inlet port is in a closed state for closing the inlet port and the closed inner space in an airtight manner;
- the absolute gas pressure inside the closed inner space, relative to a temperature of 25° C., is strictly less than the standard atmospheric pressure of 1 bar at 25° C., such that the device is able to create suction through the inlet port during a first opening of the open/close member.

According to other optional characteristics of a device according to the invention, taken alone or in combination:

- In the configuration for providing the microbiological testing device before use, the closed inner space is isolated from any external source of suction.
- The second compartment of the closed inner space is devoid of a port in fluid communication with the outside of the closed inner space.
- In the configuration for providing the device before use, the microbiological culture medium of the nutritive layer is dehydrated.

Any fluid exchange between the first and the second compartment of the closed inner space takes place through the filtration member.

The microbiological testing device comprises a support for the filtration member and the nutritive layer.

The support for the filtration member comprises a screen, for example made in the form of a perforated plate, which extends across the closed inner space between the first compartment and the second compartment.

The nutritive layer is arranged between the filtration member and the support for the filtration member.

The nutritive layer is locally secured between the filtration member and the support for the filtration member.

The support for the filtration member comprises support partitions arranged in the second compartment.

Support partitions are perforated to enable the flow of fluid on either side of said partitions in the second compartment.

A water-absorbent material is arranged in the second compartment.

The open/close member of the inlet port comprises a valve.

The open/close member of the inlet port comprises a leak-tight membrane, and the open/close member of the inlet port is brought to an open state by rupturing the membrane.

The chamber of the microbiological testing device comprises at least one main body which at least partially delimits the second compartment, and comprises a cover which at least partially delimits the first compartment, the main body and the cover being formed of separate parts assembled together to form the microbiological testing device.

The chamber of the microbiological testing device comprises at least one transparent portion.

The inlet port comprises a distributor comprising several separate passages for the liquid to be analysed.

The inlet port comprises an inner portion, which opens into the first compartment of the closed inner space, and an outer portion for connecting to a container of liquid to be analysed, and the open/close member of the inlet port is inserted between the inner portion and the outer portion of the inlet port.

In the configuration for providing the microbiological testing device before use, the absolute gas pressure inside the closed inner space is such that it enables the ingress of a predetermined volume of the sample to be analysed without discharging fluid from the inner space during the ingress of a predetermined volume of the sample to be analysed. In particular, the absolute gas pressure inside the closed inner space is preferably strictly less than the standard atmospheric pressure multiplied by the ratio of the final free volume in the inner space, after the ingress of a predetermined volume of the sample to be analysed, divided by the total volume of the inner space. In practice, in the configuration for providing the microbiological testing device before use, the absolute gas pressure inside the closed inner space is strictly less than 600 millibar absolute, preferably strictly less than 300 millibar absolute, more preferentially strictly less than 200 millibar absolute.

The invention also relates to a process for providing a microbiological testing device for testing a liquid to be analysed that is liable to contain at least one microorganism, of the type comprising providing a microbiological testing device comprising:

a chamber provided to delimit a closed inner space configured to receive the liquid to be analysed;

a microbiological filtration member, provided to be arranged in the closed inner space and to separate, in the closed inner space, a first compartment from a second compartment of the closed inner space;

an inlet port for the liquid to be analysed, the inlet port opening into the first compartment of the closed inner space, characterized in that the process comprises the provision of a nutritive layer, provided to be received inside the closed inner space and impregnated with a composition of a microbiological culture medium, the nutritive layer being in contact with the filtration member, and in that the process comprises, before any connection of the microbiological testing device to a container of liquid to be analysed, successively and in this order:

a step of depressurization to lower the absolute gas pressure inside the closed inner space;

a step of closure to close the closed inner space in an airtight manner.

The invention also relates to the use of a microbiological testing device having any one of the characteristics listed above in a process for testing a liquid to be analysed that is liable to contain at least one microorganism.

This use may also comprise the steps consisting in:

connecting a container of liquid to be analysed to the inlet port;

opening the open/close member of the inlet port to enable the passage of the liquid to be analysed from the receptacle towards the closed inner space.

It may also comprise the subsequent steps consisting in:

closing the open/close member of the inlet port;

disconnecting the container of liquid to be analysed;

incubating, in the microbiological testing device, a microorganism potentially initially contained in the liquid to be analysed.

It may comprise a further subsequent step consisting in visually detecting, counting, identifying and/or characterizing a microorganism potentially initially contained in the liquid to be analysed by viewing through a transparent portion of the chamber of the microbiological testing device.

Various other features emerge from the description below with reference to the appended drawings, which show, by way of non-limiting examples, embodiments of the subject of the invention.

FIGS. 1 to 4 depict an exemplary embodiment of a microbiological testing device 10 for testing a liquid to be analysed, said liquid being liable to contain at least one microorganism.

For the purposes of the present invention, the term microorganism covers in particular Gram-positive or Gram-negative bacteria, yeasts, amoebas, viruses and more generally single-celled organisms that are invisible to the naked eye and which can be handled and multiplied in a laboratory.

According to a preferred embodiment of the invention, the microorganism is a Gram-negative or Gram-positive bacterium or a yeast.

Figure 1:
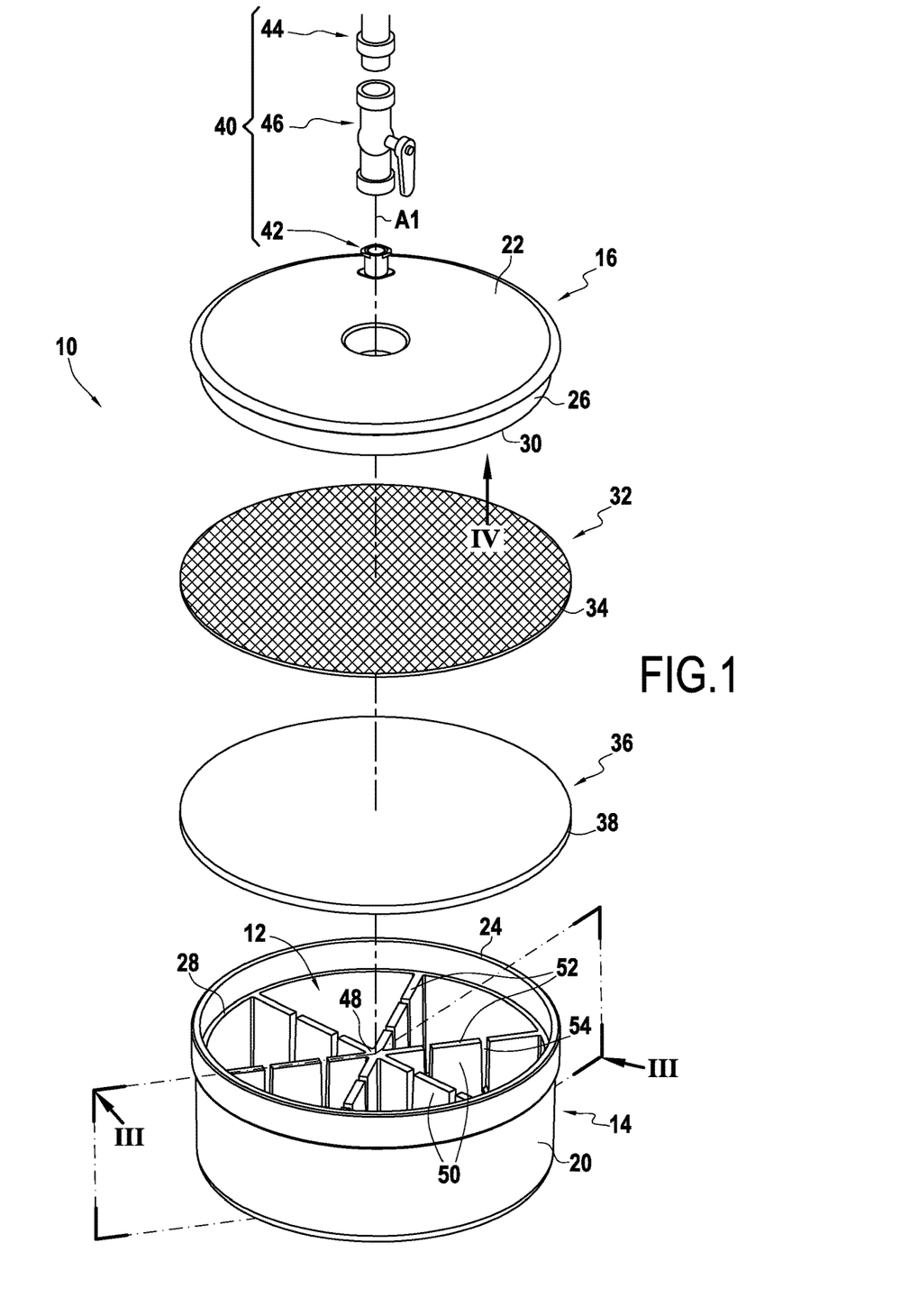
FIG. 1 is an exploded perspective view of a first exemplary embodiment of a device according to the invention.
Figure 2:
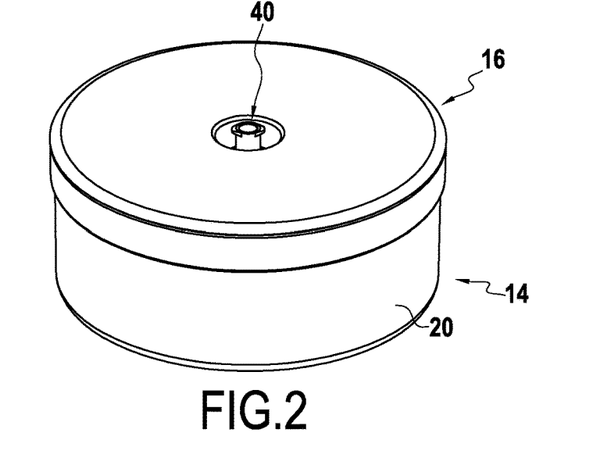
FIG. 2 is a perspective view of the device of FIG. 1, assembled.
Figure 3:
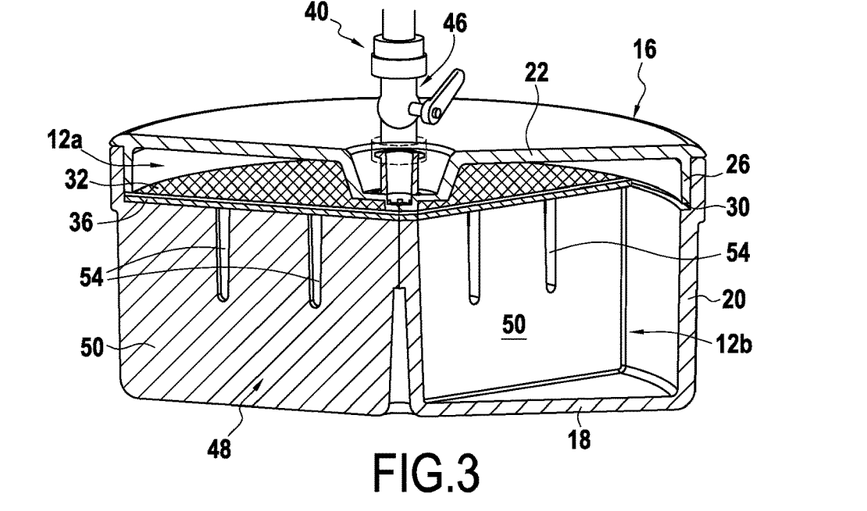
FIG. 3 is a sectional view of the device of FIG. 2, the sectional plane being illustrated in FIG. 1.
Figure 4:
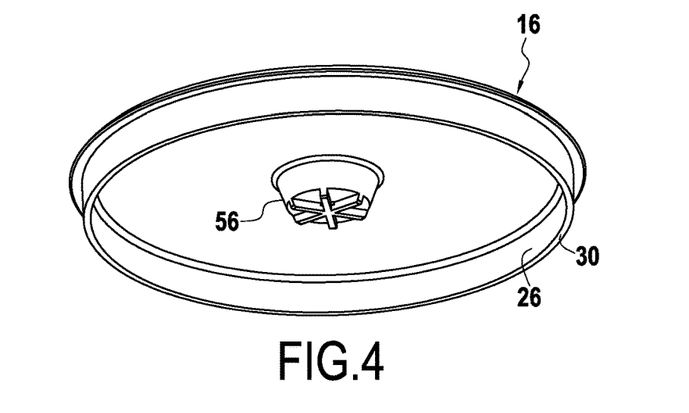
FIG. 4 is a perspective view from below of the cover of the device of FIG. 1.
Figure 5:
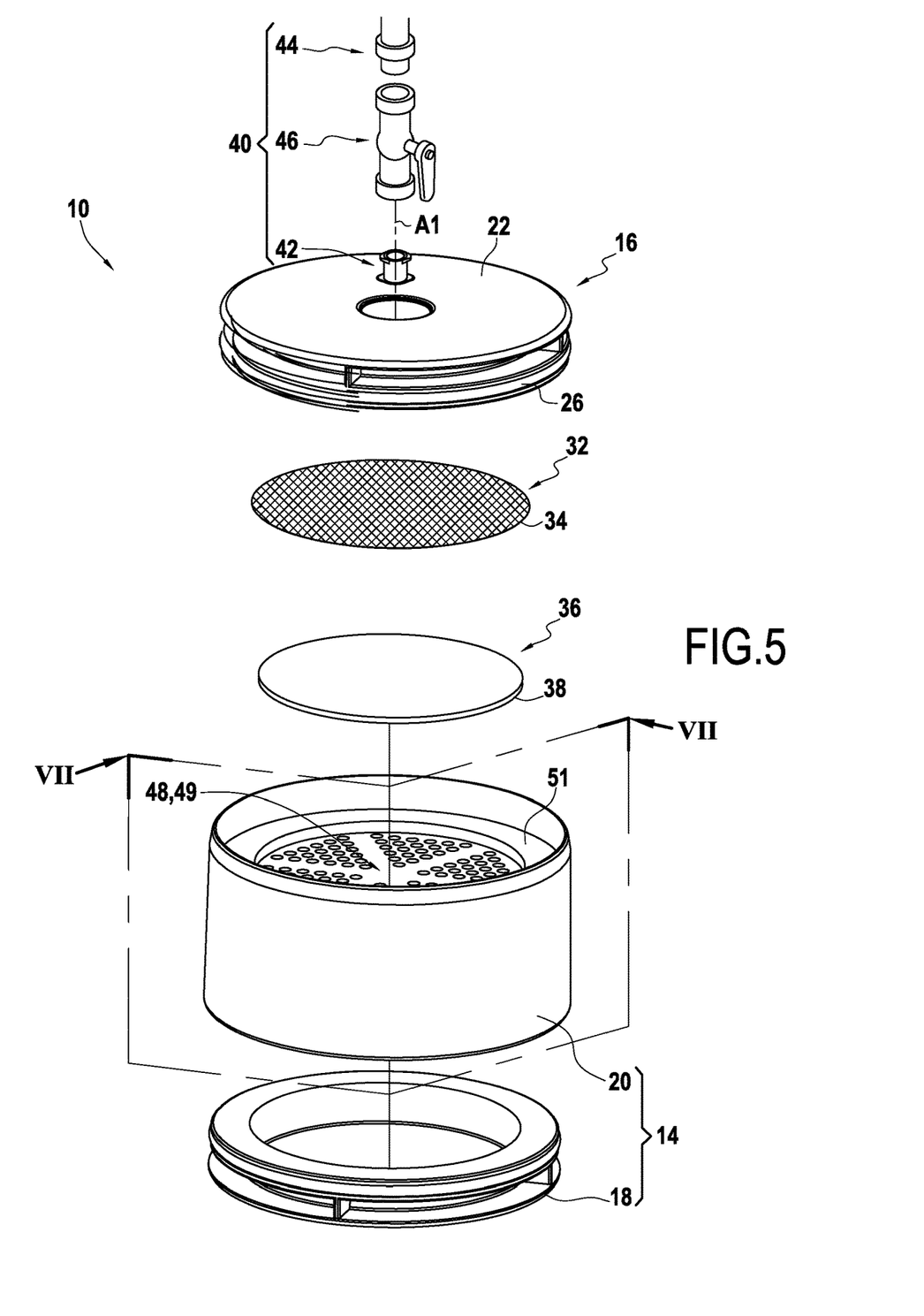
FIG. 5 is an exploded perspective view of a second exemplary embodiment of a device according to the invention.
Figure 6:
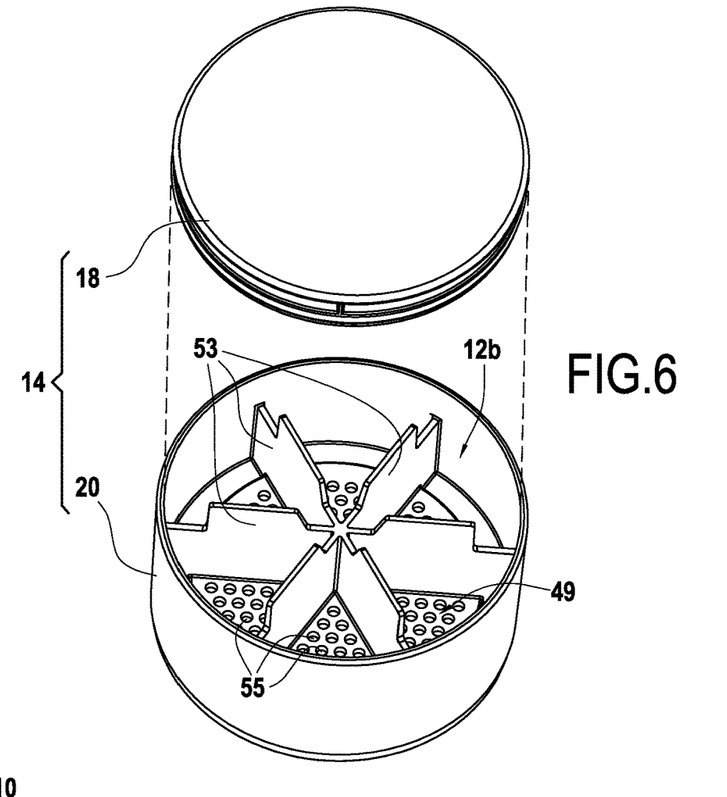
FIG. 6 is a perspective view from below of the main body and the added bottom of the second exemplary embodiment of a device according to the invention.
Figure 7:
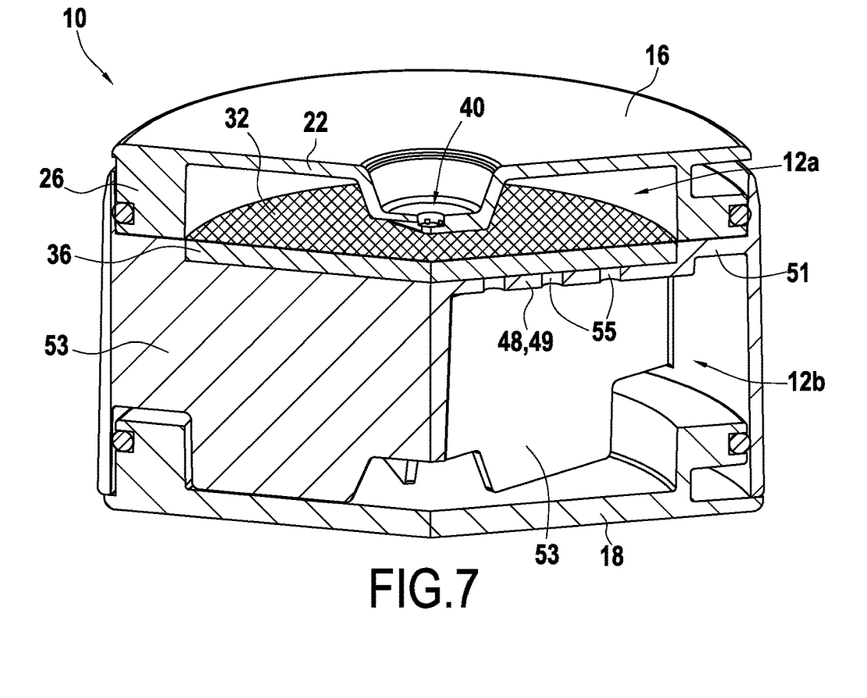
FIG. 7 is a sectional view of the device of FIG. 5, the sectional plane being illustrated in FIG. 5.

This microbiological testing device, a first exemplary embodiment of which is depicted in FIGS. 1 to 4 and a second exemplary embodiment of which is depicted in FIGS. 5 to 7, in its operational state depicted in FIGS. 2 and 3 for the first exemplary embodiment and in FIG. 7 for the second exemplary embodiment, has a closed inner space 12, delimited by a chamber and configured to receive the liquid to be analysed. The two exemplary embodiments depicted will essentially be described at the same time. The characteristics which distinguish them from one another will be mentioned as they arise.

In the depicted examples, the chamber of the microbiological testing device comprises at least one main body 14 and a cover 16. The main body 14 and the cover 16 are formed of separate parts which are assembled together to form the chamber of the microbiological testing device. The cover 16 closes the main body 14 to delimit the closed inner space 12 of the microbiological testing device 10. The cover 16 thus has a form which is complementary to that of the main body 14 in order to provide closure thereof.

In the depicted examples, the main body 14 has a bottom wall 18 and a peripheral sidewall 20 such that the main body 14 is open via an end opposite the bottom wall thereof 18. In the depicted example, the peripheral sidewall 20 has a central axis A1. The bottom wall 18 in the depicted case is a transverse wall perpendicular to the central axis A1 of the main body 14. In the first exemplary embodiment, the bottom wall 18 is produced as a single part with the peripheral sidewall 20, whereas in the second exemplary embodiment, the bottom wall 18 is produced in the form of a separate part, which closes the closed inner space 12 from the bottom. In the case in which the bottom wall 18 is produced in the form of a separate part, it may be assembled to the peripheral sidewall 20 by any known means, for example by simple snug fitting, by adhesive bonding, by welding, by screwing with clips for mechanical attachment, etc., and a seal may then be provided in order to ensure that when the bottom wall 18 is assembled to the peripheral sidewall 20, it closes the closed inner space 12 in a leak-tight manner.

For the clarity of the description, it is considered in the remainder of the description that the central axis A1 is oriented vertically and that the bottom wall 18 is arranged at a lower end of the microbiological testing device, the peripheral sidewall 20 extending upwards, along the direction of the axis A1, from the bottom wall 18. However, concepts of verticality, horizontality, and the concepts "top", "bottom", "upper", and "lower", are only used with reference to the orientation of the microbiological testing device as illustrated in the figures, relatively to one another, without having a limiting effect on the scope of the invention or the orientation of the microbiological testing device in use.

The peripheral sidewall 20 is for example a surface of revolution about the central axis A1. In the depicted example, the sidewall 20 is substantially cylindrical. However, other forms may be proposed.

Consequently, the cover 16 has a transverse wall 22, perpendicular to the central axis A1, which in this instance has a substantially circular form corresponding to the geometry of an upper edge 24 of the peripheral sidewall 20 of the main body 14. In the depicted example, the cover 16 has a cylindrical skirt 26, in this instance cylindrical of revolution about the central axis A1, which extends downwards from a lower face of the transverse wall 22 of the cover. The cylindrical skirt 26 is configured to engage, along the vertical direction of the central axis A1, inside an upper end of the peripheral sidewall 20 of the main body 14.

It is noted that, in the first exemplary embodiment, the upper end of the peripheral sidewall 20 of the main body has, on an inner face, a transverse recess which delimits an annular bearing surface 28 of central axis A1, turned upwards. The cylindrical skirt 26 has a lower edge 30, which, when the cover 16 is assembled on the main body 14, faces the annular bearing surface 28.

The microbiological testing device 10 according to the invention comprises a microbiological filtration member 32 which is arranged in the closed inner space 12 and which separates, in the closed inner space, a first compartment 12a from a second compartment 12b of the closed inner space 12.

In the depicted example, the first compartment 12a is at least partially delimited by the cover 16, while the second compartment 12b is at least partially delimited by the main body 14.

Indeed, the microbiological filtration member 32 extends in the closed inner space 12 substantially transversely along any section of the closed inner space. In the example, the microbiological filtration member 32 has a substantially planar form, in this case the form of a disk. It is preferably arranged perpendicularly to the central axis A1.

In the first depicted example, the microbiological filtration member 32 has a peripheral edge 34, which has the same form and the same dimensions as a section of the inner face of the peripheral sidewall 20 of the main body 14. In the first depicted example, the peripheral edge 34 is configured to bear axially downwards, directly or indirectly, against the annular bearing surface 28 of the main body 14. As will be seen below, in the first depicted example, the peripheral edge 34 of the microbiological filtration member 32 is preferably provided to be axially secured between the lower edge 30 of the cylindrical skirt 26 of the cover 16 and the annular bearing surface 28 of the main body 14.

The microbiological testing device comprises, inside the closed inner space 12, a nutritive layer 36 impregnated with a composition of a microbiological culture medium, the nutritive layer 36 being in contact with the microbiological filtration member 32.

In the embodiments depicted, the nutritive layer 36 is an element separate from the microbiological filtration member 32 while being in contact with the microbiological filtration member 32. The nutritive layer 36 and the microbiological filtration member 32 are brought into contact with one another within the microbiological testing device once said device is assembled.

In this case, the nutritive layer 36 is preferably located, with the provisos laid out above, below the microbiological filtration member 32. In this case, the nutritive layer 36 is located in the second compartment 12b of the closed inner space 12. However, nothing prevents providing that the nutritive layer is located, with the provisos laid out above, above the microbiological filtration member 32. In this particular case, the nutritive layer advantageously comprises at least one chromogenic and/or fluorogenic substrate which makes it possible to enable direct or indirect detection of enzymatic or metabolic activity of the target microorganisms. The visual signal generated by said at least one substrate is then visible through at least a portion of the thickness of the nutritive layer.

In the depicted examples, the nutritive layer 36 has a substantially planar form, in this case the form of a disk. The nutritive layer 36 has a peripheral edge 38, which preferably matches the peripheral edge 34 of the microbiological filtration member 32. Thus, the nutritive layer 36 and the filtration member 32 have the same form. This means that, in the first depicted example, the peripheral edge 38 can bear axially downwards against the annular bearing surface 28, being inserted between the annular bearing surface 28 of the main body 14 and the peripheral edge 34 of the microbiological filtration member 32. In the first depicted example, the peripheral edge 38 of the nutritive layer 36 is preferably provided to be axially secured, jointly with the peripheral edge 34 of the microbiological filtration member 32, between the lower edge 30 of the cylindrical skirt 26 of the cover 16 and the annular bearing surface 28 of the main body 14.

For the purposes of the present invention, the nutritive layer 36 comprises a support containing a microbiological culture medium.

The support may be based on various absorbent compounds, preferably having very high water retention ability, such as rayon, cotton, natural or chemically modified cellulose fibers such as carboxymethyl cellulose, absorbent or superabsorbent chemical polymers such as polyacrylate salts, acrylate/acrylamide copolymer. This support may be impregnated with a microbiological culture medium in liquid form. This microbiological culture medium may advantageously be dehydrated, that is to say having an "AW" (water activity) that is incompatible with microbial growth. Alternatively, the support may be covered or impregnated under dry conditions with a microbiological culture medium or the constituents thereof in powder form. Alternatively, the liquid impregnation may be supplemented by adding powder, after dehydration.

"Microbiological culture medium" is configured to mean a medium comprising the nutritional elements necessary for the survival and/or growth of microorganisms, especially one or more from carbohydrates, including sugars, peptones, growth factors, mineral salts and/or vitamins, etc. In practice, those skilled in the art will choose the microbiological culture medium as a function of the target microorganisms, according to criteria, which are perfectly well known, and within the grasp of those skilled in the art.

The nutritive layer 36 may contain optional additive elements, for instance:
  one or more selective agents such as inhibitors or antibiotics, to promote growth and development of one particular species/strain of microorganism over another;
  buffers, stains.

Generally speaking, the nutritive layer 36 may also contain a substrate enabling detection of enzymatic or metabolic activity of the target microorganisms by virtue of a directly or indirectly detectable signal. For direct detection, this substrate may be connected to a part serving as fluorescent or chromogenic label. For indirect detection, the nutritive layer according to the invention may also comprise a pH indicator, which is sensitive to the change in pH induced by consumption of the substrate and reveals the growth of the target microorganisms. Said pH indicator may be a chromophore or a fluorophore. Mention will be made, as examples of chromophores, of neutral red, aniline blue, bromocresol blue. Fluorophores include, for example, 4-methylumbelliferone, hydroxycoumarin derivatives or resorufin derivatives. Thus, the fluorescent PC-PLC substrate preferentially used for carrying out the process according to the invention corresponds to 4-MethylUmbelliferyl Choline Phosphate (4 MU-CP).

According to a preferred embodiment of the invention, the microbiological culture medium of the nutritive layer 36 is dehydrated in a configuration for providing the microbiological testing device before use. In this case, after dry impregnation of the support of the nutritive layer with the dehydrated microbiological culture medium, the nutritive layer 36 may be subject to a calendering operation. Calendering, by the pressure and heating temperature generated, enables stable retention and maintenance over time of the dehydrated microbiological culture medium in the support of the nutritive layer, ensuring the retention of the nutritional elements and of the optional additive elements in the nutritive layer.

The calendering of the nutritive layer 36 also makes it possible to obtain a smooth and flat surface of the nutritive layer. The calendering also enables acceleration of the rehydration of the nutritive layer compared to a non-calendered nutritive layer, due to the compression of the nutritive layer induced thereby. In the case in which the support is formed of fibers, this compression, combined with the presence of the dehydrated medium within the nutritive layer 36, generates a large increase in the capillary ability of said nutritive layer, causing virtually instantaneous rehydration thereof. This may also contribute to a phenomenon of suction of the separate microbiological filtration member 32 arranged against the surface thereof. The microbiological filtration member 32 may thus be pressed against the nutritive layer 36, thereby ensuring the absence of spaces or the reduction of spaces between these two, which is beneficial to optimum microbial growth and/or survival over the whole surface of the microbiological filtration member 32. It is thereby possible to avoid the presence of bonding member (for example avoid the presence of a bonding layer) between the microbiological filtration member 32 and the nutritive layer 36 when they are separate. This represents a significant advantage, insofar as such a bonding member would slow down the passage of nutritional elements and optional additive elements from the rehydrated nutritive layer 36 to the microorganisms present on the microbiological filtration member 32, thereby reducing the growth and/or the chances of survival of these microorganisms.

The microbiological filtration member 32 comprises a water-permeable filter, which retains the microorganisms, especially at the surface thereof. In the case in which the microbiological filtration member 32 is separate from the nutritive layer 36, the microbiological filtration member 32 is permeable to the nutritional elements and to the optional additive elements contained in the nutritive layer 36 located under the microbiological filtration member 32. This filter may comprise a porous body, which may be formed of a material, which, through its nature, its size, its steric arrangement, has these properties. This porous body may have these properties through the arrangement of pores.

The microbiological filtration member 32 may for example be based on one or more materials, or derivatives of these materials, from latex, polytetrafluoroethylene, poly (vinylidene) fluoride, polycarbonate, polystyrene, polyamide, polysulfone, polyethersulfone, cellulose, a mixture of celluloses and nitrocellulose. Preferentially, the microbiological filtration member 32 is produced in the form of a porous membrane permeable to the nutritional elements and the optional additive elements contained in the nutritive layer 36, and able to retain the microorganisms at the surface thereof. Preferably, the microbiological filtration member 32 covers the whole nutritive layer 36. The applicant has discovered that the currently sold microfiltration membranes for water (and generally speaking liquids) generally have the required properties to be used as microbiological filtration member 32. They make it possible to obtain good resistance to tearing during handling, controlled porosity, a smooth surface, thinness, and most of the time a high level of hydrophilicity. Their color, which is generally white, makes it possible to optimize the differentiation of colored colonies on the surface thereof. The filtration capacity and the hydrophilicity of such a filtration membrane are made use of to enable and optimize the passage of the nutritional elements and the optional additive elements present in the nutritive layer (optionally after rehydration thereof) towards an upper surface of the microbiological filtration member 32 while preventing or limiting migration in the opposite direction of the bacteria, yeasts etc., filtered at the upper surface of the microbiological filtration member 32. For the purposes of the present application, the abovementioned filtration membranes are referred to, without distinction, as "filtration membranes", "microfiltration membranes" or else "filtering membranes", these expressions being synonymous with one another. These filtration membranes are included in the group formed of porous membranes.

The microbiological filtration member 32 enables the passage of the elements of the nutritive medium and the selective agents or reagents. Advantageously, the filtration member comprises pores, the diameter of which is between 0.01 and 0.8 microns, preferentially between 0.2 microns and 0.6 microns, so as to retain bacteria, yeasts and molds on the surface thereof. According to a particular embodiment, the filtration member comprises pores, the diameter of which is between 0.25 microns and 0.6 microns, for example between 0.3 microns and 0.6 microns, or else between 0.4 microns and 0.6 microns. Alternatively, this may be a layer that does not have measurable pores, such as a dialysis membrane.

For example, a microbiological filtration member may be a "Fisherbrand™ General Filtration Membrane Filters" filtration membrane sold by Fisher Scientific Company L.L.C, 300 Industry Drive, Pittsburgh, Pa. 15275, USA, or else a "Nitrocellulose Membrane Filters" filtration membrane, manufactured by Zefon International, Inc., 5350 SW 1st Lane, Ocala, Fla. 34474, USA, or similar membranes.

In some variants, the nutritive layer may be integrated with the microbiological filtration member 32, the latter serving as support for the microbiological culture medium. In this case, it is understood that the nutritive layer is in contact with the microbiological filtration member 32.

The microbiological testing device 10 according to the invention comprises an inlet port 40 for the liquid to be analysed. The inlet port 40 makes it possible, when the microbiological testing device 10 is assembled such that the chamber delimits the closed inner space, for example when the cover 16 is assembled with the main body 14, to introduce the liquid to be analysed inside the closed inner space delimited by the chamber, originating from outside the closed inner space 12.

In the exemplary embodiments depicted, the inlet port 40 comprises an inner portion 42, which opens into the first compartment 12a of the closed inner space 12, and an outer portion 44 for connecting to a container of liquid to be analysed, the container possibly being for example a syringe, a tube, a pouch, a funnel etc.

In the depicted examples, the inlet port 40 is arranged along the central axis A1, vertically. The inlet port is advantageously arranged on the cover 16, in this instance for example in the center of the transverse wall 22 thereof.

The inner portion 42 of the inlet port 40 may comprise a distributor 56 comprising several separate passages for the liquid to be analysed. Such a distributor 56 promotes the distribution of the liquid to be analysed, which is introduced via the inlet port 40, over a larger portion of the surface area of the microbiological filtration member 32. In particular in the case of the configuration of the exemplary embodiment, the inner portion 42 of the inlet port 40 may comprise a distributor 56 which has orifices, each of which opens out at least partially along a radial direction relative to the central axis A1, the orifices preferably being distributed angularly right around the central axis A1 of the inlet port 40.

The outer connection portion 44 of the inlet port 40 may comprise element for coupling to the container. The outer connection portion 44 may itself have a funnel shape. The outer connection portion 44 may also comprise mechanical docking member for docking the container at the inlet port 40.

The microbiological testing device 10 comprises an open/close member 46 which, in the exemplary embodiments, is inserted between the inner portion 42 and the outer portion 44 of the inlet port, so as to block off the inlet port 40, preventing, in the closed state of the open/close member, any circulation of gas between the closed inner space 12 of the microbiological testing device 10 and the outside through the inlet port 40.

Preferably, the inlet port 40 is a re-closable port. In this case, which is the case depicted, the open/close member 46 may comprise a valve, Such a valve may preferably be taken successively several times from an open state to a closed state, and back again.

In some cases, the open/close member may comprise a leak-tight membrane, and the open/close member may be brought to an open state by rupturing the membrane. In this scenario, the membrane cannot be re-closed. In this case, it may be possible to re-close the inlet port 40 by a secondary open/close member added to the outer connection portion 44. Such a secondary open/close member (not shown) may for example be formed by a cap, a leak-tight membrane, or a stopper.

It will be noted that such a secondary open/close member may also be provided in the case of the presence of an open/close member of valve type as mentioned above. Such a secondary open/close member for example makes it possible to reinforce the gas-tightness of the valve, especially the airtightness, and especially the long-term gas-tightness during a period of storage of the device 10 before use.

In both cases, such a secondary open/close member makes it possible to protect the inlet port from any contamination during a period of storage of the device 10 before use.

In the examples depicted, the microbiological testing device 10, once assembled, only comprises a single port for fluid communication between the closed inner space 12 and the outside, in this case the inlet port 40. In the example depicted, it will be noted that the second compartment 12b of the closed inner space 12 is devoid of a port in fluid communication with the outside of the closed inner space. However, this does not prevent the microbiological testing device 10 from being able to comprise several ports for fluid communication, including the inlet port 40, all opening into the first compartment 12a of the closed inner space.

In the exemplary embodiments, the microbiological filtration member 32 has a small thickness relative to the extent thereof. For example, the diameter of the filtration member is greater than 50 millimeters, for example between 80 and 100 millimeters. The thickness thereof is of the order of a few millimeters, generally less than 5 millimeters.

It is also advantageous to provide for the microbiological testing device 10 to comprise a support 48 for the microbiological filtration member 32 and for the nutritive layer 36.

The support 48 makes it possible to hold the microbiological filtration member 32 and the nutritive layer 36 in their position between the first compartment 12a and the second compartment 12b.

In the first exemplary embodiment depicted, the support 48 for the microbiological filtration member 32 and for the nutritive layer 36 comprises support partitions 50 arranged in the second compartment 12b.

For example, the support partitions 50 may be of planar form, each arranged in a radial plane containing the central axis A1. They may for example extend from the bottom wall 18 of the main body 14 and have an upper edge 52 against which the microbiological filtration member 32 and the nutritive layer 36 may bear vertically downwards, directly or indirectly. In the first example depicted, each support partition 50 extends diametrically through the whole of the second compartment 12b, thus being limited transversely by two diametrically opposed portions of the peripheral sidewall 20 of the main body 14. In this particular embodiment, it is understood that the support partitions 50 carry out their support function via their upper edge 52. In the example depicted, the upper edges 52 of the support partitions 50 all extend in the same transverse plane perpendicular to the central axis A1.

Nonetheless, amongst themselves, the support partitions 50 delimit amongst themselves, in the second compartment 12b, subdivisions of this second compartment 12b. Such support partitions 50 may be perforated to enable the flow of fluid on either side of said partitions in the second compartment 12b. In the example depicted, it is chosen to provide the support partitions 50 with through-openings 54, which enable fluid communication between two adjacent subdivisions of the second compartment 12b, which are separated by one of these support partitions 50. These through-openings 54 are optional. In the example depicted, they are produced in the form of slits, which extend along the direction of the central axis A1 from a low point located substantially halfway up the second compartment 12b, and they open out in an open manner in the upper edge 52. These through-openings may have a different geometry altogether and for example be produced in the form of holes, especially circular holes. They do not necessarily open out into the upper edge 52.

In the example depicted, the support partitions 50 also make it possible to mechanically reinforce the chamber of the device, especially to make it more resistant to a difference in pressure between the inside and the outside of the chamber.

The support 48 for the microbiological filtration member 32 could be produced differently. It could for example be produced in the form of a screen extending in a transverse plane perpendicular to the central axis A1. Such a screen could for example be supported by bearing on the bearing surface 28 of the main body 14. The support for the microbiological filtration member 32 could be produced in the form of one or more columns extending vertically along the direction of the axis A1 from the transverse bottom wall 18 of the main body 14. The support for the microbiological filtration member 32 could also be produced in the form of one or more brackets extending transversely from an inner face of the peripheral sidewall 20.

In the second example depicted in FIGS. 5 to 7, the support 48 for the filtration member comprises a screen 49. Such a screen could be formed by a network of criss-crossing wires or by a network of criss-crossing bars. In the example depicted in FIGS. 5 to 7, the screen is formed by a perforated plate, which extends perpendicular to the central axis A1 between the first compartment and second compartment. This screen 49 is, in the depicted case, produced as a single part with the peripheral sidewall 20 of the main body 14. It is understood that this screen 49 in the form of a perforated plate provides better support for the microbiological filtration member 32, especially if the latter is not very stiff. This results in better flatness of the microbiological filtration member 32 and of the nutritive layer 36, especially when carrying out the filtration process.

In the example depicted, the plate extends through the main body 14 over the entire internal diameter thereof. The plate has an annular outer peripheral portion 51, which extends radially towards the central axis A1 from an inner cylindrical surface of the peripheral sidewall 20. The outer peripheral portion 51 of the plate is solid, i.e. not perforated. The plate has a perforated central portion, in the center of this outer peripheral portion, which forms the screen 49. The upper face of the perforated central portion 49 is offset downwards relative to an upper surface of the outer peripheral portion. In this way, the outer peripheral portion 51 delimits, in the upper face of the plate, a recess, the diameter of which corresponds to that of the perforated central portion 49. In the example depicted, the filtration member 32 and the nutritive layer 36 have an outer diameter, which is equal to, or less than the diameter of the recess. Thus, the filtration member 32 and the nutritive layer 36 can be accommodated in the recess, being radially wedged in the recess. It is noted that, in this second exemplary embodiment, the filtration member 32 and the nutritive layer 36 are not gripped between the cover 16 and the main body 14, unlike the first exemplary embodiment.

It is noted that in FIG. 6, in the view from below, the second exemplary embodiment comprises, in the second compartment 12b, partitions 53, which, aside from the function of direct support of the filtration member, have the same functions and substantially the same geometry as the support partitions of the first exemplary embodiment.

The support 48 is dimensioned to form limited, or even negligible, resistance to the flow of the fluids between the first and the second compartment of the closed inner space. In the case of a perforated plate, it will be ensured for example that the cumulative total surface area in projection along the central axis A1 of the perforations 55 represents at least 30% of the surface area of the filtration member 32, preferably at least 50% of the surface area of the filtration member. The perforated plate has a multitude of perforations 55, distributed inside a defined circle (smaller circle containing all the perforations) which is in correspondence with at least 50%, preferably at least 70% of the surface area of the filtration member 32. In the envisioned examples, the perforations 55 are greater than 20, preferably greater than 50, in number. However, with larger perforations, and optionally with different geometry, for example star-shaped, fan-shaped, etc., a lower number of perforations could be used.

In the example depicted, the support 48 for the microbiological filtration member 32 is produced as a single part with the main body 14. However, this support could be produced in the form of one or more independent parts. Such parts may simply be placed inside the second compartment 12b or may be assembled to the main body 14, for example by adhesive bonding, by welding, by snap fastening or by interlocking.

In the example depicted, it is noted that the nutritive layer 36 is arranged between the microbiological filtration member 32 and the support 48 for the filtration member.

Advantageously, it is possible to provide for the nutritive layer 36 to be locally secured between the microbiological filtration member 32 and its support 48. For example, the cover 16 may comprise bearing elements, corresponding for example to the upper edge of one or more of the support partitions 50, such that, when the microbiological testing device is assembled, the microbiological filtration member 32 and the nutritive layer 36 are secured between these bearing elements of the cover 16 and the support 48. In the example depicted, the distributor 56 has, on a lower face, such bearing element for clamping the microbiological filtration member 32 and the nutritive layer 36 against the support 48 in the center of the microbiological testing device.

In the example depicted, the volume of the second compartment 12b of the closed inner space 12 is greater than the volume of the first compartment 12a of the closed inner space. Preferably, the volume of the second compartment 12b of the closed inner space 12 is at least two times, preferably at least three times, greater than the volume of the first compartment 12a of the closed inner space. In one embodiment, for a device configured for the analysis of a 100-milliliter sample, the volume of the second compartment 12b of the closed inner space 12 is for example at least 100 milliliters, preferably greater than 100 milliliters and less than 150 milliliters, in order to be able to contain all of the volume of a liquid to be analysed. The total volume of the closed inner space delimited by the chamber is for example between 120 and 300 milliliters, this total volume being for example 150 milliliters.

In a configuration for providing the microbiological testing device 10 before use, the open/close member 46 is in a closed state to close the inlet port 40 and the closed inner space 12 in an airtight manner.

In this configuration for provision, the microbiological testing device 10 is thus closed in a leak-tight manner, without possible gas communication between the closed inner space 12 delimited by the chamber and the outside. In this configuration for provision, the microbiological filtration member 32 and the nutritive layer 36 are contained inside this closed inner space 12 delimited by the chamber, thereby forming a ready-to-use microbiological testing device for filtering the liquid to be analysed in order to collect potential microorganisms therefrom on the microbiological filtration member 32 and to enable the growth of these microorganisms with a view to detection, counting, characterization and/or identification.

Moreover, in this configuration for providing the microbiological testing device 10 before use, the absolute gas pressure inside the closed inner space is at a reduced initial pressure value such that the device is able to create suction through the inlet port during a first opening of the open/close member 46.

The result of the two previous paragraphs is that, in this configuration for providing the microbiological testing device 10 before use, therefore before any introduction of a sample into this closed inner space 12 delimited by the chamber, the microbiological filtration member 32 and the nutritive layer 36, which comprises a composition of a microbiological culture medium, are contained inside this closed inner space 12 delimited by the chamber and the absolute gas pressure inside the closed inner space is at a reduced initial pressure value such that the device is able to create suction through the inlet port during a first opening of the open/close member 46.

For this purpose, the reduced initial pressure value of the absolute gas pressure inside the closed inner space (12), relative to a temperature of 25° C., is strictly less than the standard atmospheric pressure of 1 bar at 25° C.

In practice, this phenomenon of suction will be reflected by a quicker ingress into the inner space of the device of a predetermined volume of liquid during the first opening of the open/close member than in the case in which the initial pressure in the inner space is equal to atmospheric pressure.

It will be noted that it is not necessary to precisely know the precise value of the reduced initial pressure. Indeed, this value is above all determined so as to be sufficient to suck at least part, or even all, of a predetermined volume of the sample to be analysed inside the device.

Preferably, this value is determined so as to be sufficient for the device to be able to suck the entirety of a predetermined volume of the sample to be analysed inside the device, without it being necessary to subject the sample to be analysed to a pressure greater than standard atmospheric pressure in order to cause it to enter inside the device.

Preferably, this reduced initial pressure value is sufficiently low to enable the ingress of the entirety of a predetermined volume of the sample to be analysed into the inner space without discharging fluid from the inner space during the ingress of the predetermined volume of the sample to be analysed. This makes it possible to ensure easy ingress of the whole sample into the device. This also makes it possible to avoid any propagation of elements initially contained in the device, especially elements of the culture medium, to the outside during the ingress of the sample into the device.

Those skilled in the art will be able, by an initial evaluation optionally supplemented with a few tests, to determine a desired reduced initial pressure for the device, as a function of the conditions envisioned for using the device (total volume of the closed inner space 12 delimited by the chamber of the device, volume of the sample, temperature and pressure conditions when using the device, etc.).

The desired reduced initial pressure can be practically evaluated in the following manner. The total volume VT of the closed inner space 12 delimited by the chamber is considered. A predetermined volume VE of the sample to be analysed, which it is desired to be able to introduce into the device 10 to carry out the analysis, is subsequently determined. The final free volume VL in the inner space after the ingress of the predetermined volume of the sample to be analysed into the inner space is subsequently deduced therefrom. This final free volume VL is therefore equal to the total volume VT of the closed inner space 12 delimited by the chamber, from which is subtracted the predetermined volume VE of the sample to be analysed which it is desired to be able to introduce into the device 10 to carry out the analysis:

$$VL=VT-VE$$

The ideal gas law is then applied, as an approximation, to the variations in conditions in the closed inner space 12 delimited by the chamber between the moment just before the ingress of the sample and the moment just after the ingress of this sample, assuming that only liquid containing the sample is introduced without significant variations in temperature. This ingress of the sample is reflected by a variation in the pressure from the reduced initial pressure value Pi, which is the value of the absolute gas pressure inside the closed inner space in the configuration for provision, to a final value Pf, which is the absolute gas pressure value inside the inner space after the ingress of a predetermined volume of the sample to be analysed.

The following equation is therefore obtained $$Pf \times VL = Pf \times (VT-VE) = Pi \times VT$$

which gives $$Pi = Pf \times (VT-VE)/VT = Pf \times VL/VT$$

It is deduced therefrom that, in the configuration for providing the microbiological testing device 10 before use, the absolute gas pressure inside the closed inner space 12, referred to as reduced initial pressure, is preferably strictly less than the atmospheric pressure multiplied by the ratio of the final free volume in the inner space, after the ingress of a predetermined volume of the sample to be analysed, divided by the total volume of the inner space.

The value of the standard atmospheric pressure can be practically arbitrarily fixed at 1 bar at 25° C.

In practice, it is generally considered that a sample must have a volume VE of at least 20 milliliters, preferably at least 50 milliliters, more preferentially at least 100 milliliters. On the other hand, it is generally considered that a sample must have a volume VE of 300 milliliters or less, preferably 200 milliliters or less, more preferentially 150 milliliters or less.

In the case of a device, the total volume VT of the inner space of which is 150 milliliters, and for a sample of volume VE of 100 milliliters, the quick calculation above gives the desired reduced initial pressure, for the absolute gas pressure inside the closed inner space 12 in the configuration for providing the device before use, of strictly less than 333 millibar absolute. However, in practice, it will be preferable to provide a reduced initial pressure of strictly less than 300 millibar absolute, to take into account approximations associated with the difference between the hypotheses formulated and experimental reality. More preferentially, it will be preferable to provide an initial pressure of strictly less than 200 millibar absolute, especially to promote rapid ingress of the sample into the device.

It will be noted that, for a total volume VT of 300 milliliters of the inner space of the device, a desired reduced initial pressure of strictly less than 666 millibar absolute is thus determined, preferably strictly less than 600 millibar absolute, more preferentially strictly less than 400 millibar absolute.

It is noted that the values above are indicative values, including for a given device and given conditions of use. Indeed, it would be even better for the reduced initial pressure in the device to actually be lower than the above values.

In practice, these values will be able to serve as a basis for developing a device according to the invention, and the manufacturing conditions enabling the correct operation of the device will be easily determined with a few routine tests.

Thus, the above values may be measured by connecting a manometer to the inlet of the inlet port, as close as possible to the open/close member 46, even if this results in an uncertainty as to the actual value of the reduced initial pressure, including if this uncertainty is as much as 50 millibar.

This means that, when preparing the microbiological testing device, an at least partial vacuum is created in the closed inner space. This at least partial vacuum may for example have been created by assembly under vacuum, or at least under a pressure less than or equal to the desired reduced initial pressure, in any case strictly less than 1 bar at 25° C., or by depressurization of the closed inner space after assembly of the microbiological testing device.

It is understood that, in this configuration for providing the microbiological testing device 10 before use, the closed inner space is isolated from any external source of suction. This therefore explains the necessity to provide that the chamber and the inlet port 40 in the closed state thereof are gas-tight, especially airtight. This is obtained by any means known to those skilled in the art.

In the example depicted, the cover 16 and the main body 14 are thus assembled in an airtight manner.

The assembly may be an assembly, which can be dismantled, enabling opening of the microbiological testing device without destruction after use thereof, for example in order to remove the microbiological filtration member 32. An assembly, which can be dismantled, may be produced for example using complementary threads arranged respectively on the cover 16 and the main body 16. In the depicted configuration, such complementary threads (not shown) may be fitted respectively on an outer face of the cylindrical skirt 26 of the cover 16 and on an inner face of the upper end of the peripheral sidewall 20 of the main body 14. Another possible example of an assembly, which can be dismantled, may be obtained by a system of bayonet assembly. Yet another example of an assembly, which can be dismantled, may be obtained by providing an external assembly flange or by providing screws for assembling the cover 16 on the main body 14.

The assembly may be an assembly, which cannot be dismantled, not enabling opening of the microbiological testing device 10 without destruction after use thereof, for example by adhesive bonding, by welding or by riveting.

In order to provide the required gas-tightness, especially airtightness, it is possible to provide, especially in the case of an assembly, which can be dismantled, one or more seals (not shown) between the main body 14 and the cover 16.

In the configuration for providing the microbiological testing device before use, the microbiological culture medium of the screen layer 36 is advantageously dehydrated. It is then provided that this microbiological culture medium is rehydrated at the time of use. This rehydration may be carried out by the liquid to be analysed itself.

Indeed, the microbiological filtration member 32 and the nutritive layer 36 are arranged such that any fluid exchange between the first compartment 12a and the second compartment 12b of the closed inner space occurs through the microbiological filtration member 32 and the nutritive layer 36. It is thus possible to make it impossible for a fluid to bypass either the microbiological filtration member 32 or the nutritive layer 36 to pass from the first compartment 12a to the second compartment 12b. In the embodiment depicted, this arises from the fact that the microbiological filtration member 32 and the nutritive layer 36 extend through the whole of the section of the closed inner space 12 of the microbiological testing device between the first compartment 12a and the second compartment 12b of the closed inner space.

Advantageously, it may be provided that a water-absorbent material is arranged in the second compartment. In the example depicted, such a material may be arranged in one, several, or all of the subdivisions of the second compartment 12b between the support partitions 50. An absorbent material may be based on various absorbent compounds, preferably having very high water retention ability, such as rayon, cotton, natural or chemically modified cellulose fibers such as carboxymethyl cellulose, absorbent or superabsorbent chemical polymers such as polyacrylate salts, acrylate/acrylamide copolymer. Such materials may thus be obtained from Technical Absorbents Limited, 1 Moody Lane, Great Coates, Grimsby, DN31 2SS, United Kingdom, under the trade name "Super Absorbent Fibre (SAF®)".

The chamber of the microbiological testing device may advantageously be made of polymeric material. However, it is also possible to make it from other materials, including at least partially from glass. In the example depicted, the main body 14, the cover 16 and the support 48 may be made of the same material, or of different materials.

Preferably, the chamber of the microbiological testing device comprises at least one transparent portion. In particular, this transparent portion may be arranged such that an observer can see at least a portion of the upper face of the microbiological filtration member 32 which is turned towards the first compartment 12a. Preferably, this transparent portion is arranged such that an observer can see all of the upper face of the microbiological filtration member 32, which is turned, towards the first compartment 12a. This is because it is on this face that any potential microorganisms will be visible after incubation. In the example depicted, the transparent portion of the chamber is therefore preferably arranged at least in the transverse wall 22 of the cover 16. The whole of the cover 16 may be transparent. In some embodiments, it will be provided that the whole of the chamber is made of transparent material. The transparent portion of the chamber is for example made of poly(methyl methacrylate) (PMMA) or glass.

A microbiological testing device as described above is therefore configured to be used in a process for testing a liquid to be analysed that is liable to contain at least one microorganism.

In such a use, a microbiological testing device is provided beforehand in a configuration for provision before use. As was seen above, in this configuration, the microbiological testing device has the microbiological filtration member 32 and the nutritive layer 36 which are contained in the closed inner space 12 in a leak-tight manner, and in this closed inner space a level of negative pressure prevails which corresponds to the reduced initial pressure, in any case to an absolute gas pressure inside the closed inner space, relative to a temperature of 25° C., of strictly less than 1 bar.

In order to provide a microbiological testing device for testing a liquid to be analysed that is liable to contain at least one microorganism, it is first of all necessary to provide a microbiological testing device comprising, as described above:
  a chamber provided to delimit a closed inner space 12 configured to receive the liquid to be analysed, for example in the form of a main body 14 and a cover 16;
  a microbiological filtration member 32 provided to be arranged in the closed inner space 12 and to separate, in the closed inner space, a first compartment 12a from a second compartment 12b of the closed inner space;
  an inlet port 40 for the liquid to be analysed, provided to open out into the first compartment 12a of the closed inner space, the inlet port being able for example to comprise an inner portion 42 provided to open out into the first compartment 12a of the closed inner space, and an outer connection portion 44.

Moreover, the process for provision before use comprises the provision of a nutritive layer 36, provided to be received inside the closed inner space and comprising a composition of a microbiological culture medium, the nutritive layer 36 being configured to be in contact with the filtration member. As seen above, this nutritive layer 36 may be separate from the microbiological filtration member 32 or, as a variant, it is possible to provide that the nutritive layer and the microbiological filtration member are integrated with one another.

According to the invention, the process for provision of the microbiological testing device in a configuration for provision comprises, before any use, therefore before any connection to a container of liquid to be analysed, successively and in this order:
  a step of depressurization to lower the absolute gas pressure inside the closed inner space 12;
  a step of closure to close the closed inner space 12 in an airtight manner.

It is noted that at the time of the depressurization step, the microbiological testing device 10 comprising the elements described above may be already assembled, such that the chamber is closed and contains the above elements. In this case, the depressurization step may be carried out by connecting the closed inner space 12 of the microbiological testing device to a source of suction, for example a vacuum pump, for example through the inlet port 40, the latter thus being in an open state. Thereby, the pressure is lowered to the desired reduced initial pressure which is, in any case, relative to a temperature of 25° C., strictly less than 1 bar.

In another variant, the depressurization step may be concomitant to an assembly step. Indeed, in the example depicted, it is possible to provide for example that the assembly of the cover 16 on the main body 14, which makes it possible to close the chamber and thus to delimit the closed inner space 12, may be carried out under an absolute gas pressure equal to or less than the desired reduced initial pressure, i.e. especially a pressure, relative to a temperature of 25° C., of strictly less than 1 bar.

In the first case, the step of closure may consist in closing a valve of the inlet port 40 or placing a sealing membrane, as long as there is still an absolute gas pressure equal to or less than the desired reduced initial pressure. In the second case, the step of closure may consist in assembling the cover 16 on the main body 14 in a leak-tight manner which makes it possible to close the chamber. In this case, the open/close member of the inlet port 40 is preferably previously in a closed state.

Thus, a microbiological testing device 10 is obtained in a configuration for provision in which, inside the closed inner space 12 delimited by the chamber, the microbiological filtration member 32 and the nutritive layer 36 are located, the closed inner space 12 being at a predetermined initial level of negative pressure, referred to as reduced initial pressure, and which corresponds to a gas pressure in the closed inner space which is less than a predetermined threshold, the predetermined threshold itself being strictly less than standard atmospheric pressure, the predetermined threshold being for example 200 millibar of absolute pressure relative to 25° C.

It is noted that, in this configuration for provision, the microbiological testing device may be stored, transported, etc., and that in this configuration for provision, no liquid to be analysed has been introduced into the closed inner space 12 of the microbiological testing device.

The use of a microbiological testing device according to the invention corresponds to the introduction of the liquid to be analysed inside the closed inner space 12 via the inlet port 40. This introduction generally corresponds to the connection of a container, in which the liquid to be analysed is found, to the inlet port 40. Such a connection may take various forms, simply assuming that a fluid connection is established between the container and the inlet port 40. Preferably, this connection is a fluid-tight connection, and preferably a gas-tight, especially airtight connection. This connection may comprise mechanical docking between the container and the inlet port 40.

Thus, the use of a microbiological testing device according to the invention comprises the steps consisting in:
- connecting a container of liquid to be analysed to the inlet port 40, especially in the exemplary embodiment to the outer connection portion 42 of the inlet port 40;
- opening the open/close member 46 of the inlet port to enable the passage of the liquid to be analysed from the container towards the closed inner space 12 of the microbiological testing device.

This step of opening the open/close member 46 of the inlet port is a first opening of the open/close member following a step of closure for closing the closed inner space 12 in a leak-tight manner during the process for provision.

It is in this step that the predetermined initial level of negative pressure has a particularly important role. Indeed, the presence of this negative pressure promotes the introduction of the liquid to be analysed into the closed inner space 12 of the microbiological testing device. This is due on the one hand to the phenomenon of suction exerted on the liquid to be analysed if the latter is initially for example at atmospheric pressure. This is due on the other hand to the fact that the predetermined level of negative pressure is reflected by the presence of a small amount of gas in the microbiological testing device before the introduction of the liquid to be analysed, such that the microbiological testing device, during the introduction of the liquid to be analysed, does not have to discharge a corresponding amount of gas. Not only does this facilitate the ingress of the liquid to be analysed into the closed inner space of the microbiological testing device, but it also avoids the expulsion of particles or molecules initially contained in the microbiological testing device to the outside.

It is noted that during this step of use of the microbiological testing device during which the opening of the open/close member enables the passage of the liquid to be analysed from the container to the closed inner space 12, the closed inner space 12 may be isolated from any external source of suction. Indeed, the suction is advantageously obtained by virtue of the reduced initial pressure present in the device before the first opening of the device following a step of closure to close the closed inner space 12 in an airtight manner during the process for provision.

Thus, the introduction of the liquid to be analysed into the microbiological testing device 10 according to the invention through the inlet port 40 enables the liquid to be introduced firstly into the first compartment 12a of the closed inner space 12, the liquid to be analysed then naturally coming into contact with the microbiological filtration member 32. The liquid to be analysed is thus filtered through this microbiological filtration member 32 such that at least some of the potential microorganisms, especially those targeted for the envisioned testing, are retained by the microbiological filtration member 32. On the other hand, the liquid portion of the liquid to be analysed migrates towards the second compartment 12b of the closed inner space 12. For this, it is understood that it is advantageous for the microbiological testing device, for this step at least, to be in the orientation illustrated in the figures, the second compartment 12b of the closed inner space 12 being located below the first compartment, the two compartments being separated from one another by the microbiological filtration member 32 which, in the example depicted, extends along a plane which is then horizontal.

The liquid to be analysed enables the rehydration of the nutritive layer 36. Since the nutritive layer 36 is in contact with the filtration member, the nutritive elements and the optional additive elements thereof may migrate towards the microorganisms which are retained by the microbiological filtration member 32. Thus, should the microbiological testing device 10 be placed in a favorable environment, especially temperature, it is possible to obtain incubation of the microorganisms inside the microbiological testing device 10 itself, without it being necessary to open the latter, in any case without it being necessary to remove the microbiological filtration member 32 from the chamber of the microbiological testing device 10.

Thus, the use of a microbiological testing device 10 according to the invention may, after the step of introduction of a liquid to be analysed inside the closed inner space 12 of the microbiological testing device, comprise the subsequent steps consisting in:
- closing the open/close member 46 of the inlet port 40;
- incubating, in the microbiological testing device, a microorganism potentially initially contained in the liquid to be analysed.

After such a period of incubation, the use may comprise a subsequent step consisting in visually detecting, counting, identifying and/or characterizing a microorganism potentially initially contained in the liquid to be analysed, especially by viewing through a transparent portion of the chamber of the microbiological testing device. Here also, this testing step may be carried out without it being necessary to open the microbiological testing device 10, the microbiological filtration member 32 on which the potential microorganisms are located, thus remaining inside the closed inner space of the microbiological testing device 10.

The invention is not limited to the examples described and depicted, since various modifications may be made thereto without departing from the scope thereof.

The invention claimed is:

1. A microbiological testing device in a configuration before use for testing a liquid liable to contain at least one microorganism, comprising:
- a closed inner space delimited by a chamber and configured to receive the liquid;
- a microbiological filtration member arranged in the closed inner space and separating, in the closed inner space, a first compartment from a second compartment of the closed inner space;
- an inlet port for the liquid that opens into the first compartment of the closed inner space;
- a nutritive layer comprising a composition of a microbiological culture medium inside the closed inner space and in contact with the filtration member;
- an open/close member that closes the inlet port and the closed inner space in an airtight manner; and
- an absolute gas pressure inside the first compartment and the second compartment of the closed inner space, relative to a temperature of 25° C., that is strictly less than standard atmospheric pressure of 1 bar at 25° C., such that suction is created through the inlet port during a first opening of the open/close member,
- wherein the second compartment of the closed inner space is devoid of a port in fluid communication with an outside of the closed inner space.

2. The microbiological testing device as claimed in claim 1, wherein the closed inner space is isolated from any external source of suction.

3. The microbiological testing device as claimed in claim 1, wherein the microbiological culture medium of the nutritive layer is dehydrated.

4. The microbiological testing device as claimed in claim 1, further comprising a support for the filtration member and the nutritive layer.

5. The microbiological testing device as claimed in claim 4, wherein the nutritive layer is locally secured between the filtration member and the support.

6. The microbiological testing device as claimed in claim 4, wherein the support comprises support partitions arranged in the second compartment.

7. The microbiological testing device as claimed in claim 4, wherein the support comprises a screen which extends across the closed inner space between the first compartment and the second compartment.

8. The microbiological testing device as claimed in claim 1, further comprising a water-absorbent material arranged in the second compartment.

9. The microbiological testing device as claimed in claim 1, wherein the open/close member comprises a valve that closes the inlet port.

10. The microbiological testing device as claimed in claim 1, wherein the chamber comprises at least one main body which at least partially delimits the second compartment, and comprises a cover which at least partially delimits the first compartment.

11. The microbiological testing device as claimed in claim 1, wherein the chamber comprises at least one transparent portion.

12. The microbiological testing device as claimed in claim 1, wherein the inlet port comprises a distributor comprising several separate passages for the liquid.

13. The microbiological testing device as claimed in claim 1, wherein the absolute gas pressure inside the closed inner space enables ingress of a predetermined volume of the liquid without discharging fluid from the inner space during the ingress of the predetermined volume of the liquid.

14. The microbiological testing device as claimed in claim 1, wherein the absolute gas pressure inside the closed inner space is strictly less than the standard atmospheric pressure multiplied by a ratio of final free volume in the inner space, after ingress of a predetermined volume of the liquid, divided by total volume of the inner space.

15. The microbiological testing device as claimed in claim 1, wherein the absolute gas pressure inside the closed inner space, relative to the temperature of 25° C., is strictly less than 600 millibar absolute.

16. A process for depressurizing and closing the microbiological testing device according to claim 1 so as to obtain the configuration before use for testing the liquid, comprising:

lowering the absolute gas pressure inside the inner space, relative to the temperature of 25° C., to strictly less than 1 bar to depressurize the first compartment and the second compartment of the inner space; and closing the open/close member so as to seal the inlet port and the inner space in the airtight manner.

17. The process as claimed in claim 16, wherein the absolute gas pressure inside the closed inner space enables ingress of a predetermined volume of the liquid without discharging fluid from the inner space during the ingress of the predetermined volume of the liquid.

18. The process as claimed in claim 16, wherein the absolute gas pressure inside the closed inner is a value strictly less than the standard atmospheric pressure multiplied by a ratio of final free volume in the inner space, after ingress of a predetermined volume of the liquid, divided by total volume of the inner space.

19. The process as claimed in claim 16, wherein the absolute gas pressure inside the closed inner space, relative to the temperature of 25° C., is a value strictly less than 600 millibar absolute.

20. A process for testing the liquid using the microbiological testing device as claimed in claim 1, comprising:

connecting a container of the liquid to the inlet port; and opening the open/close member to pass the liquid from the container into the inner space of the microbiological testing device.

21. The process as claimed in claim 20, further comprising:

closing the open/close member after passage of the liquid from the container into the inner space of the microbiological testing device;

disconnecting the container from the inlet port; and incubating the microbiological testing device to grow any microorganism from the liquid on the nutritive layer after passage of the liquid through the filtration membrane.

22. The process as claimed in claim 21, further comprising visually detecting, counting, identifying and/or characterizing the microorganism if grown on the nutritive layer by viewing the nutritive layer through a transparent portion of the chamber of the microbiological testing device.

* * * * *